(12) United States Patent
Carano et al.

(10) Patent No.: US 6,921,395 B2
(45) Date of Patent: Jul. 26, 2005

(54) LIQUID SPECIMEN COLLECTION SYSTEM

(75) Inventors: Donald J. Carano, Pequannock, NJ (US); Raymond T. Wasek, Monroe Township, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 145 days.

(21) Appl. No.: 10/222,747

(22) Filed: Aug. 16, 2002

(65) Prior Publication Data

US 2003/0036742 A1 Feb. 20, 2003

Related U.S. Application Data

(60) Provisional application No. 60/313,046, filed on Aug. 17, 2001.

(51) Int. Cl.[7] ............................. A61B 19/00; A61M 1/00
(52) U.S. Cl. ........................ 604/411; 604/321; 604/326; 604/415
(58) Field of Search ............................... 604/317, 321, 604/326, 411, 415; 215/347, 329, DIG. 3; 220/288, 254.1, 254.7, 255

(56) References Cited

U.S. PATENT DOCUMENTS

| | | | |
|---|---|---|---|
| 3,392,859 A | * | 7/1968 | Fischer ..................... 215/247 |
| 3,653,528 A | | 4/1972 | Wimmer |
| 3,904,482 A | * | 9/1975 | Mehl ......................... 435/34 |
| 4,116,066 A | * | 9/1978 | Mehl et al. .............. 73/864.52 |
| 4,244,478 A | * | 1/1981 | Handman .................. 215/249 |
| 4,258,032 A | | 3/1981 | Mehl |
| 4,300,404 A | | 11/1981 | Mehl et al. |
| 4,336,880 A | | 6/1982 | Mehl |
| 4,726,950 A | | 2/1988 | Desai et al. |
| 4,768,653 A | | 9/1988 | Desai et al. |
| 4,886,071 A | * | 12/1989 | Mehl et al. ................. 600/573 |
| 5,312,009 A | | 5/1994 | Ratajczak et al. |
| 6,203,503 B1 | * | 3/2001 | Kelly et al. ................. 600/573 |
| 6,255,101 B1 | * | 7/2001 | Rousseau et al. ......... 435/288.1 |
| 6,354,603 B1 | * | 3/2002 | Villette ....................... 277/637 |
| 6,382,441 B1 | * | 5/2002 | Carano ....................... 215/247 |
| 6,391,014 B1 | * | 5/2002 | Silverman ................... 604/415 |
| 6,571,837 B2 | * | 6/2003 | Jansen et al. ............... 141/329 |
| 6,599,273 B1 | * | 7/2003 | Lopez ......................... 604/249 |
| 6,601,721 B2 | * | 8/2003 | Jansen et al. ............... 215/249 |
| 2002/0079284 A1 | * | 6/2002 | Carano ....................... 215/247 |
| 2004/0108293 A1 | * | 6/2004 | Brockwell .................. 215/247 |

FOREIGN PATENT DOCUMENTS

| | | |
|---|---|---|
| EP | 0642830 | 3/1995 |
| EP | 0901824 | 3/1999 |

* cited by examiner

*Primary Examiner*—Larry I. Schwartz
*Assistant Examiner*—Michael G. Bogart

(57) ABSTRACT

A container assembly provides for the collection, transporting, and dispensing of a fluid specimen. The container assembly includes a cup-shaped container having an open end for collecting the fluid specimen. A lid is attachable to the container to close the open end thereof. The lid includes an access port for providing communication with the collected fluid specimen through the cover and for permitting extraction of a sample therefrom. A self-sealing closure member is supported by the lid in the access port and seals the access port preventing fluid leakage. The extraction device may be used to extract a sample of the fluid specimen. The extraction device is insertable through the self-sealing closure to permit such extraction. Upon removal of the extraction device, the self-sealing closure recloses the access port.

7 Claims, 3 Drawing Sheets

LIQUID SPECIMEN COLLECTION SYSTEM

This application claims the benefit of Provisional Application No. 60/313,046, filed Aug. 17, 2001.

BACKGROUND OF THE INVENTION

1. Field of the Invention

The present invention relates generally to a container used for collecting, transporting and dispensing a biological fluid specimen. More particularly, the present invention relates to a cup-shaped container which accommodates a liquid specimen such as a urine specimen and which provides a sealable passage for insertion of a specimen extracting device.

2. Description of Related Art

In order to conduct laboratory testing on biological fluid samples such as urine, it is necessary to provide a container for collecting urine specimens. These specimen collection containers typically include a cup-shaped container with a removable cover. Once the sample has been collected in the container, the cover is reapplied. The specimen collection container may then be transported to a laboratory or other testing facility where a sampling of the collecting specimen is extracted for test purposes.

In an effort to simplify the sample extraction process, the prior art has seen the use of covers which not only cover and seal the collection container, but also provide for the use of an extraction device which permits the extraction of a sample of the fluid specimen. Such covers may support a tube which extends from the cover to the lower end of the cup-shaped container in fluid communication with the specimen contained therein. The tube may include at its upper end a needle which extends above the cover so that at an air-evacuated collection container, such as a specimen collection tube, may be attached thereto to draw a portion of the collected sample thereinto without removal of the cover. Subsequent samples may be drawn from the specimen collection container by using plural collection tubes.

Once the desired number of samples are drawn, the specimen collection container must be discarded in a safe and appropriate manner. The disposal of these specimen collection containers may pose certain biohazards. For example, as noted, the cover includes a tube with a needle at one end for piercing the septum of the air evacuated collection tube. Thus, the specimen collection container must be safely discarded as a sharps device. This greatly increases the time and cost of the disposal.

Furthermore, as the needle and tube in the cover provide for fluid communication for externally drawing the collected specimen, there is the risk of specimen leakage during the transport and disposal process.

It is, therefore, desirable to provide an improved specimen collection container which safely collects, transports and dispenses a fluid specimen and which can be easily and safely discarded after use.

SUMMARY OF THE INVENTION

The present invention is directed to a container assembly for collecting, transporting and dispensing a fluid specimen. The container assembly preferably includes a cup-shaped container having an open end for collecting the fluid specimen. A lid is attachable to the container to close the open end of the container. The lid includes an access port for providing communication with the collected fluid through the cover. A self-sealing closure member is supported by the cover in the access port and permits sealed insertion of an extraction therethrough.

More preferably, the container assembly of the present invention includes a closure member for the access port of the lid which is an elastomeric stopper having resiliently deflectable walls. The walls are deflectable to allow insertion of the extraction device.

More preferably, the stopper may include an upper surface having a slit diaphragm defining the deflectable walls.

Still further, the stopper may include an upper surface wherein the deflectable walls extend downwardly from the upper surface.

In a preferred embodiment, the extraction device may include a fluid drawing tube which is elongate having one end extendible through the cover into the cup-shaped container into fluid communication with the fluid contained therein. The opposite end of the tube may include a needle cannula which is used to pierce the septum of an air-evacuated specimen collection tube. The extraction device is insertable through the stopper on the lid. Once the fluid specimen is drawn, the extraction device is removed and discarded as a sharps device. The rubber stopper seals the opening in the lid and the container assembly may be safely and easily transported and discarded in an appropriate manner.

DETAILED DESCRIPTION

The present invention provides an assembly for collecting, transporting, dispensing and disposing of a biological fluid specimen. The present invention more particularly permits the collection of biological specimens such as a urine specimen in a collection container and permits the extraction of a sample specimen from the container. The remaining urine sample may be discarded in the container in a safe and efficient manner.

Figure 1:
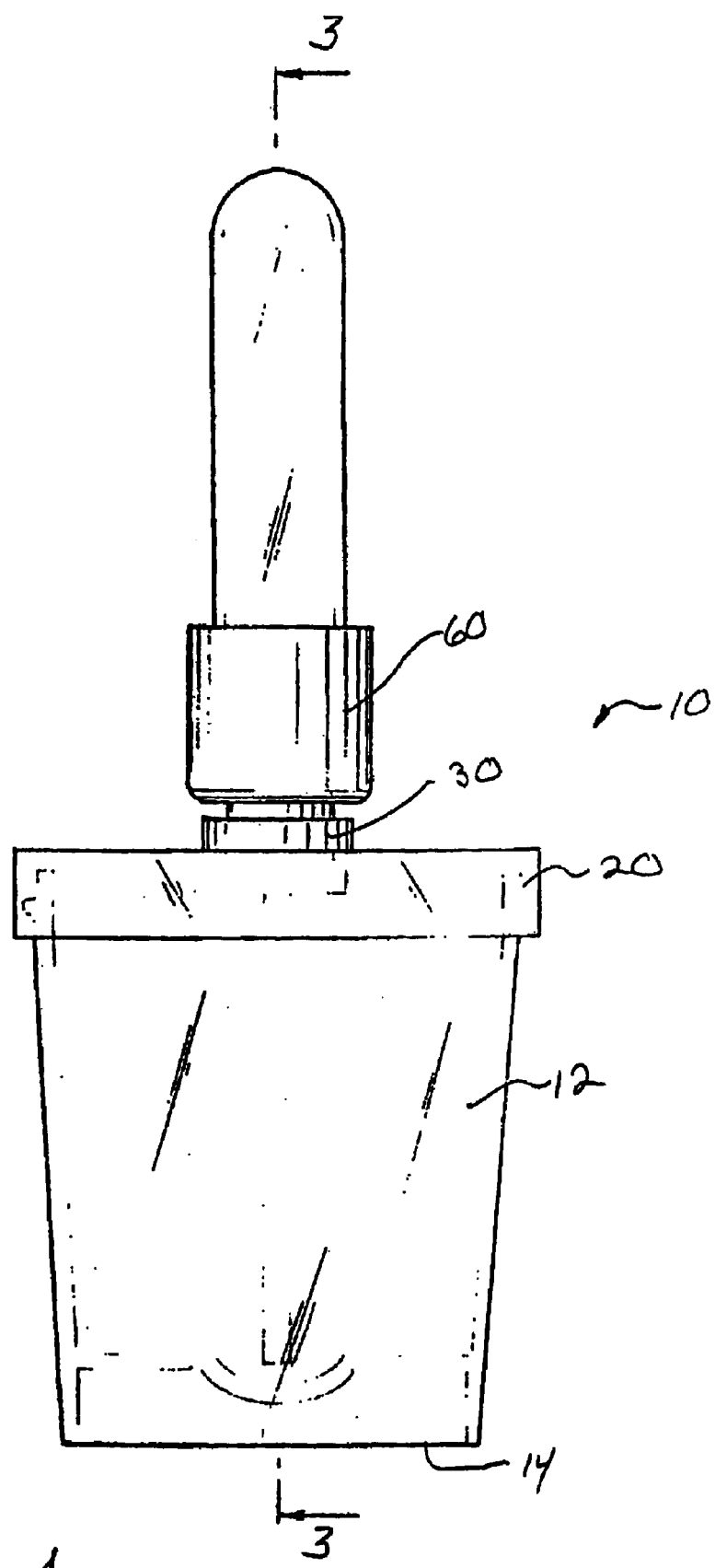
FIG. 1 is a side elevational showing of the fluid specimen collection assembly of the present invention.
Figure 2:
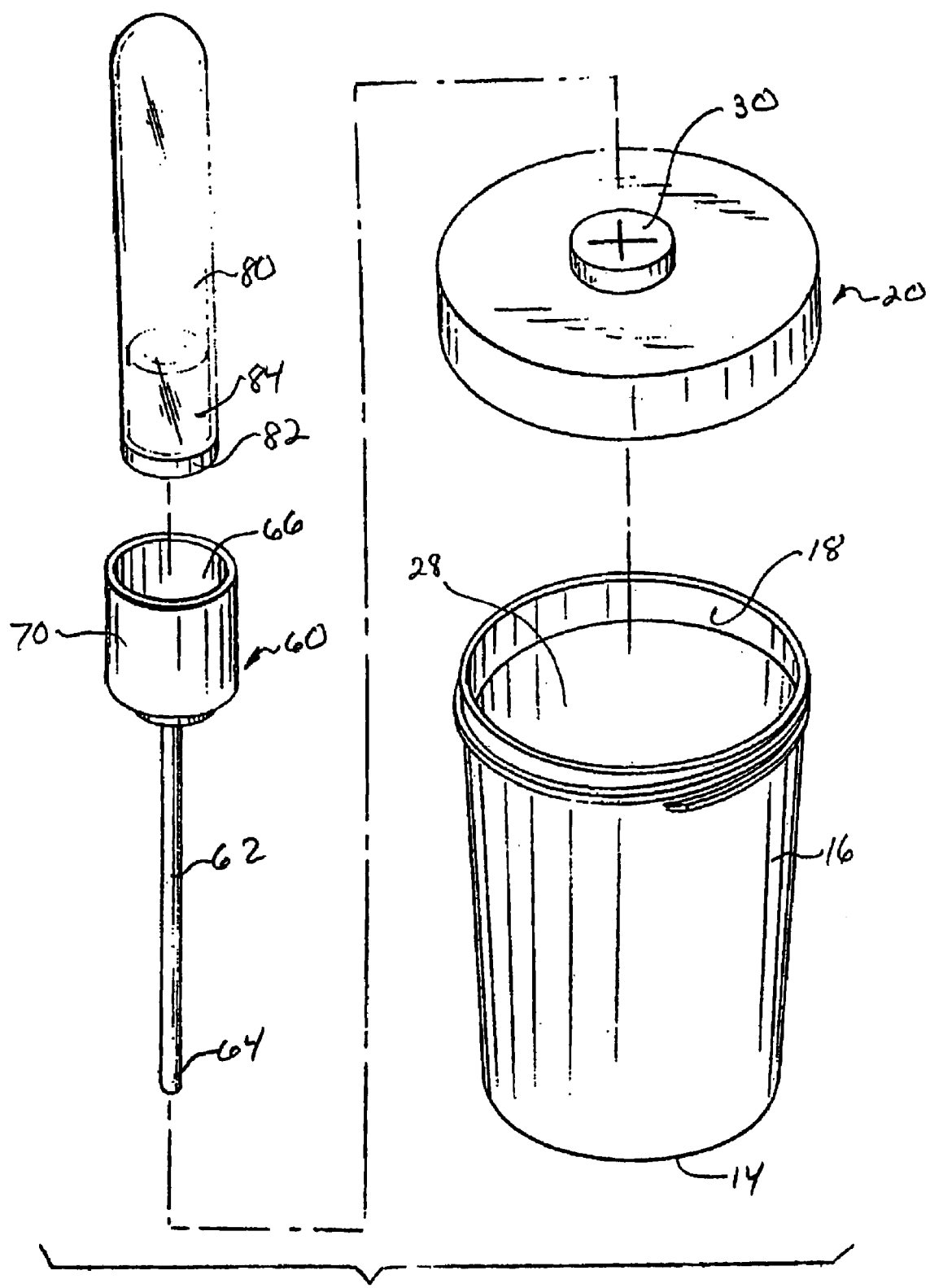
FIG. 2 is an exploded perspective showing of the fluid specimen collection assembly of FIG. 1.
Figure 3:
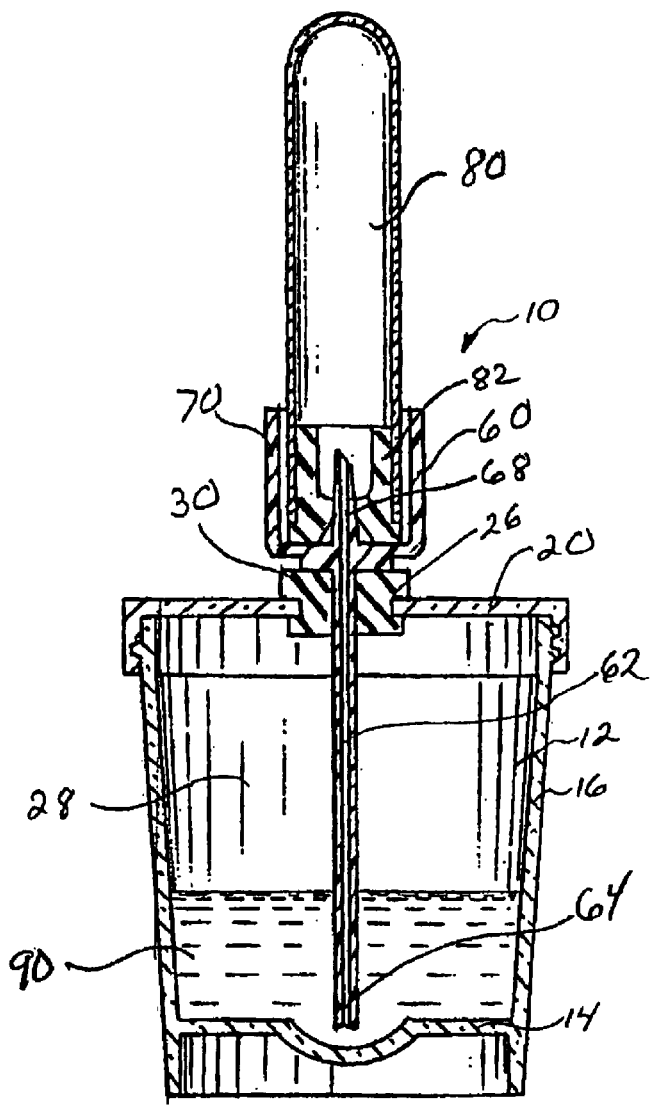
FIG. 3 shows in vertical sectional showing of the collection assembly of FIG. 1.

Referring now to FIGS. 1–3, the present invention provides collection assembly 10 used to collect, transport, dispense and dispose of a liquid specimen such as a urine specimen. Assembly 10 includes a cup-shaped container 12 having a closed bottom wall 14, a generally upstanding cylindrical side wall 16 and an open upper end 18. The upper edge of side wall 16 may be externally screw threaded. Cup-shaped container 12 may be formed of a transparent plastic or any other suitable material.

Assembly 10 further includes a lid 20 for attachment to the open end of container 12. Lid 20 has a flat planar upper surface 22 and a depending annular skirt 24 which is internally screw threaded for screw accommodation onto the upper end 18 of container 12.

The upper surface 22 of lid 20 includes a centrally located generally circular access port 26 extending therethrough.

The access port provides communication to the interior 28 of container 12 through lid 20.

In order to sealably close access port 26, the present invention provides a resilient elastomeric stopper 30 which may be attached to lid 20 and interposed within access port 26. The stopper 30 is generally a resilient elastomeric self-sealing member which permits insertion of a an extraction device therethough. As will be described in further detail hereinbelow, stopper 30 provides for sealed engagement with an extraction device upon insertion and also provides for self-sealing upon removal of the extraction device therefrom.

While any self-sealing elastomeric stopper may be employed, two preferred embodiments of the elastomeric stopper 30 are shown.

Figure 4:
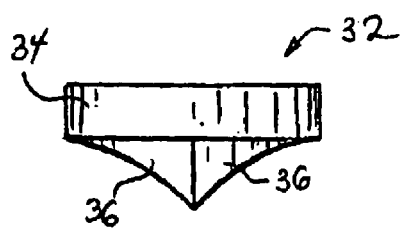
FIGS. 4 and 5 show a side elevation and a top plan view respectively of one embodiment of the elastomeric stopper used in accordance with the collection assembly of FIG. 1.
Figure 5:
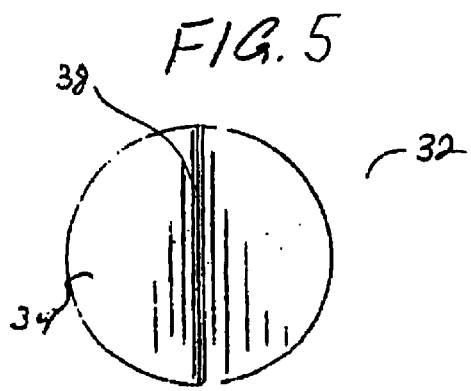

Referring to FIGS. 4 and 5, a first configuration referred to as a "duck bill" stopper 32 is shown. The stopper 32 includes an annular upper portion 34 having a diameter which is slightly greater than the diameter of access port 26. The stopper 32 further includes a pair of deflectable walls 36 which extend downwardly from annular upper portion 34. Walls 36 are resiliently deformable and are provided in sealed engagement. The walls define a longitudinal slit 38 at the surface 35 of upper portion 34 as viewed in FIG. 5. The slit defines the engagement between the walls 36. The slit is pierceable by an inserted extraction device so as to spread the walls 36 apart permitting insertion. The walls are resiliently deformable so that the walls seal around the device inserted therethough providing a seal therebetween. Upon removal of the device, the walls elastomerically return to the original position in sealed engagement. The elastomeric stopper 32 may be force fitted onto lid 20 (FIG. 3) in conventional fashion filling access port 26 so as to provide a sealed closure thereat.

Figure 6:
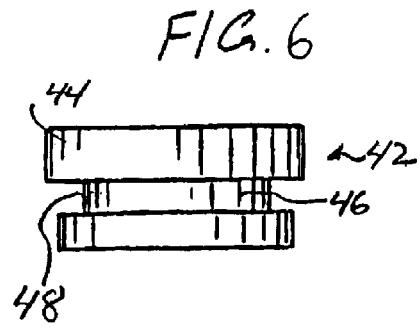
FIGS. 6 and 7 show respectively a side elevation and a top plan view of a further embodiment of the elastomeric closure used in combination with the collection assembly of FIG. 1.
Figure 7:
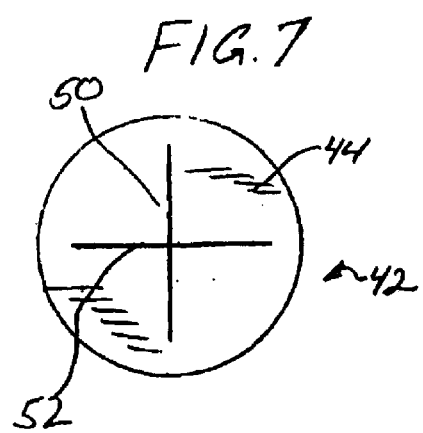

Referring to FIGS. 6 and 7, a further embodiment referred to as a "diaphragm" stopper 42 is shown. Diaphragm stopper 42 also includes an annular upper surface 44 and a depending portion 46 extending downwardly therefrom. The depending portion is generally annular in configuration and includes an undercut 48 externally thereabout. The undercut 48 permits retention of the stopper 42 within the access port 26 of lid 20. As particularly shown in FIG. 5, the annular upper portion 44 of stopper 42 includes a diaphragm 50 defined by a cross shaped slit 52. The slit 52 defines walls of the diaphragm which are resiliently deflectable to permit insertion of an extraction device therethrough. As with stopper 30, the diaphragm 50 of stopper 42 provides sealed engagement with the inserted device. Upon removal of the inserted device, the diaphragm closes in a self-sealing manner.

While FIGS. 4–7 show two embodiments of a self-sealing rubber stopper, other stopper constructions are within the contemplation of the present invention.

Referring again to FIGS. 1–3, the collection assembly 10 of the present invention further includes an extraction device 60 which permits the extraction of a sample of the urine specimen collected within container 12. Extraction device 60 includes an elongate hollow fluid extraction tube 62 having a distal end 64 for insertion within container 12 and a proximal end 66 for positioning externally thereof. The proximal end 66 may include a piercing needle cannula 68 formed threat. The piercing needle cannula 68 is designed for piercing engagement through a rubber closure 82 of an air-evacuated sample collection tube 80.

The extraction device 60 further includes a cup-like receptacle 70 which provides for the accommodation of the end 84 of the collection tube. The needle cannula 68 and the elongate tube 62 are in fluid communication so as to provide a path for the extraction of a urine specimen from container 12.

Having described the components of the collection assembly of the present invention, its use in collecting, transporting, and disposing of a urine specimen can now be described.

Referring to the drawings, the container 12 of assembly 10 of the present invention may be used to collect a urine specimen 90 therein. Once the urine specimen 90 is deposited within the interior 28 of container 12, the lid 20 may be screw attached to the open upper end 18 thereof. As the lid includes rubber stopper 30 therein, the lid and container provide for sealed engagement of collected urine specimen. Urine specimen 90 may be now safety transported to laboratory or other test facility where a sample of the urine specimen may be extracted for testing.

In order to extract a sample of urine specimen 90, the laboratory technician inserts extraction device 60 into container 12 through rubber stopper 30 positioned within lid 20. As described above, the resiliency of stopper 30 ensures that the stopper is in sealed engagement with the extraction device upon insertion. This minimizes the risk of spillage during the extraction process. In conventional fashion, an air evacuated specimen collection tube 80 having a pierceable rubber stopper 82 is inserted into the cup-like receptacle 70 such that the needle cannula 68 at the end of tube 62 is in piercing engagement through the rubber stopper 82. As the collection tube 80 is air evacuated, a sample of the urine specimen 90 is drawn through tube 62 into the specimen collection tube. After the desired amount of a urine sample is collected within the collection tube 82, the tube may be removed and subsequent specimen collection tubes may be inserted to draw additional urine samples.

After the desired number of samples have been attained, the extraction device 60 may be removed. As the extraction device 60 includes a piercing needle cannula, the extraction device itself may be discarded in an appropriate manner as a sharp device. Once the extraction device 60 is removed, the rubber stopper 30 self-seals, thereby effectively preventing leakage of any remaining urine sample therefrom. As the extraction device 60 has been removed and discarded, remaining assembly 10 can be easily discarded in an appropriate manner without the necessity of treating the assembly as a sharp device.

Various other changes and modifications may be effected therein by one skilled in the art without departing from the scope and spirit of the invention, and is intended to claim all such changes and modifications as fall within the scope of the invention.

What is claimed is:

1. An assembly for the collecting, transporting, dispensing and disposing of a biological fluid specimen comprising:

a cup-shaped container having an upper open end and a container interior for collecting said fluid specimen;

a lid removably attachable to said upper open end of said container to enclose said collected fluid specimen, said lid having an access port therethrough;

a self-sealing closure member supported by said lid within said access port including an elastomeric stopper having resiliently deflectable walls sealing said access port; and an elongate extraction device removably insertable through said port, said extraction device having one end in fluid communication with said collected specimen and an opposed end for pierceable engagement with an evacuated specimen collection tube, said extraction device being in said engagement with said closure member, with said closure member being self-sealing upon removal of said extraction device therefrom.

2. An assembly of claim 1 wherein said resiliently deflectable walls seal against said extraction device upon insertion.

3. An assembly of claim 1 wherein said extraction device includes an elongated hollow tube, said to be having a first end extendible into said container interior and a second end exteriorly accessible.

4. An assembly of claim 3 wherein said second end includes a needle cannula for said pierceable engagement with said evacuated specimen collection tube.

5. An assembly of claim 4 wherein said extraction device includes a cup-shaped receptacle about said needle cannula for receipt of said evacuated specimen collection tube.

6. The assembly of claim 1, wherein said opposed end of said extraction device comprises a piercing needle cannula.

7. A kit for collecting, transporting, and dispensing of a biological fluid sample, comprising:

a cup-shaped container having an upper open end for collecting said fluid specimen;

a removably attachable lid configured so as to engage said upper end of said cup-shaped container, said lid having an access port therethrough;

a self-sealing closure member supported by said lid within said access port; and an elongate extraction device removably insertable through said self-sealing closure member, whereby said extraction device includes a first blunt end for fluid communication with a collected specimen and a second sharp end for pierceable engagement with an evacuated specimen collection tube.

* * * * *